(12) United States Patent
Lappe et al.

(10) Patent No.: US 7,317,128 B2
(45) Date of Patent: Jan. 8, 2008

(54) PROCESS FOR PREPARING TCD-DIAMINE

(75) Inventors: Peter Lappe, Dinslaken (DE); Helmut Springer, Dinslaken (DE); Rainer Lukas, Essen (DE)

(73) Assignee: Oxea Deutschland GmbH, Oberhausen (DE)

( * ) Notice: Subject to any disclaimer, the term of this patent is extended or adjusted under 35 U.S.C. 154(b) by 429 days.

(21) Appl. No.: 10/967,597

(22) Filed: Oct. 18, 2004

(65) Prior Publication Data

US 2005/0101796 A1    May 12, 2005

(30) Foreign Application Priority Data

Nov. 8, 2003    (DE) .................. 103 52 258

(51) Int. Cl.
*C07C 209/00*    (2006.01)
(52) U.S. Cl. ...................... 564/445; 564/446
(58) Field of Classification Search ................ 564/445, 564/446
See application file for complete search history.

(56) References Cited

U.S. PATENT DOCUMENTS 5,041,675 A * 8/1991 Lukas et al. ................ 564/446

FOREIGN PATENT DOCUMENTS

| DE | 29 28 313 | 2/1981 |
| EP | 0 186 075 | 7/1986 |
| EP | 0 811 424 A2 | 12/1997 |
| EP | 1 065 194 A1 | 1/2001 |

OTHER PUBLICATIONS

XP-002306531 Chem.Abstracts Serv. 1999, (4 Pages).
XP-002306410 Chem. Abstracts Serv. 1981 (2 Pages).

* cited by examiner

*Primary Examiner*—Reitsang Shiao
(74) *Attorney, Agent, or Firm*—Charles A. Muserlian

(57) ABSTRACT

A process for preparing 3(4),8(9)-bis(aminomethyl)tricycle-[5.2.1.0$^{2,6}$]decane by hydroformylating dicyclopentadiene with subsequent reductive amination wherein the hydroformylation of dicyclopentadiene is carried out in two stages, and, in a first hydroformylation stage, the reaction is effected in a heterogeneous reaction system using an aqueous solution of transition metal compounds, containing water-soluble organic phosphorus (III) compounds in complex-bound form, of group VIII of the Periodic Table to give 8(9)-formyltricyclo[5.2.1.0$^{2,6}$]dec-3-ene, and, in a second hydroformylation stage, the thus obtained 8(9)-formyltricyclo[5.2.1.0$^{2,6}$]dec-3-ene is converted, in a homogeneous organic phase in the presence of transition metal compounds of group VIII of the Periodic Table of the Elements to 3(4),8(9)-bisformyltricyclo[5.2.1.0$^{2,6}$]decane

13 Claims, No Drawings

PROCESS FOR PREPARING TCD-DIAMINE

The present invention relates to a process for preparing TCD-diamine {3(4),8(9)-bis(aminomethyl)tricyclo[5.2.1.0$^{2,6}$]decane} from dicyclopentadiene (DCP).

Dicyclopentadiene (DCP), readily available by dimerizing cyclopentadiene and also prepared on the industrial scale, can be converted to compounds having important applications, to which the tricyclodecane structure imparts particular properties. The compounds, derived from DCP, having tricyclodecane structure are frequently named differently in the literature. Based on the nomenclature for DCP derivatives, disclosed by Chemiker-Zeitung, 98, 1974, pages 70 to 76, the nomenclature building on the tricyclodecane structure, also known as TCD structure, is also used hereinbelow.

Especially the hydroformylation of DCP affords TCD-aldehydes of interest, such as 8(9)-formyltricyclo[5.2.1.0$^{2,6}$]dec-3-ene, also referred to as TCD-monenal, or 3(4),8(9)-bisformyltricyclo[5.2.1.0$^{2,6}$]decane, also referred to as TCD-dialdehyde, which are further processed to give important intermediates. Owing to their thermal lability which leads to losses in the course of distillation, the TCD-aldehydes are usually not isolated in pure form, but rather further processed as crude products of the hydroformylation reaction. For instance, the reductive amination of TCD-dialdehyde to TCD-diamine {3(4),8(9)-bis(aminomethyl)tricyclo[5.2.1.0$^{2,6}$]decane}, which finds use as a valuable intermediate in numerous syntheses performed industrially, for example for preparing light-resistant polyurethane systems (DE 28 19 980), for producing dental materials (WO 2002 013 767, EP 678 533), for synthesizing polyamides (EP 168 816), polyfunctional epoxy resin systems (JP 58 135 875), thermally curable coating materials (EP 59 962), epoxy resin hardeners (JP 54 004 992), and for preparing TCD-diisocyanate (NL 66 14 717).

The preparation of aldehydes by catalytic addition of carbon monoxide and hydrogen to olefinic double bonds is known. While this reaction has previously been carried out virtually exclusively using Co as a catalyst, modern processes work with metallic rhodium or with rhodium compounds as catalysts which are used alone or with complex-forming ligands, for example organic phosphines or esters of phosphorous acid. There is unanimous agreement in the technical field that active catalysts under the reaction conditions are hydridocarbonyl compounds of rhodium which can be expressed by the formula H[Rh(CO)$_{4-x}$L$_x$] where L denotes a ligand and x is 0 or an integer from 1 to 3.

A special case is the hydroformylation of dienes. While the hydroformylation of conjugated dienes under the customary conditions of the oxo process provides almost exclusively monoaldehydes, it is possible to obtain not only the mono- but also the disubstitution products from dicyclopentadiene (DCP) with its isolated double bonds. Owing to the risk of a retro-Diels-Alder reaction at the temperatures of the oxo process and the associated release of Cyclopentadiene which is capable of complex formation with transition metals and can reduce the activity of the catalysts used, the hydroformylation has to proceed under special conditions. It has been found to be advantageous to replace the formerly customary cobalt catalyst with rhodium, which allows a high selectivity of the conversion to aldehydes to be achieved and allows the hydroformylation under conditions under which the extent of retro-Diels-Alder dissociation is lower. A review of the hydroformylation of dicyclopentadiene and of the further processing of TCD-aldehydes can be found in Chemiker-Zeitung 98, 1974, 70-76.

The preparation of TCD-diamine is disclosed by EP-A2-0 348 832. According to this, dicyclopentadiene is hydroformylated in organic solution in the presence of rhodium to give crude TCD-dialdehyde which is subsequently reductively aminated in a second reaction step without further removal of the TCD-dialdehyde and without removal of the catalyst. According to the known procedure, the problems which are associated with the difficult removal of the reactive TCD-dialdehyde from the hydroformylation mixture are circumvented. This is because the thermal treatment of the very reactive TCD-dialdehyde during the distillative removal leads to considerable product losses.

According to JP 10 087 573, TCD-diamine is prepared by hydrogenating the corresponding TCD-dialdehyde dioxime in the presence of Fe—Cr-modified Ra-nickel.

The known processes enable the preparation of TCD-diamine in only economically moderate selectivities and yields. There is therefore a need for a very simple and inexpensive process for hydroformylating DCP with subsequent preparation of TCD-diamine.

The invention therefore consists in a process for preparing 3(4),8(9)-bis(aminomethyl)tricyclo[5.2.1.0$^{2,6}$]decane by hydroformylating dicyclopentadiene with subsequent reductive amination. The process comprises reacting dicyclopentadiene, in a first hydroformylation stage in a heterogeneous reaction system using an aqueous solution of transition metal compounds, containing water-soluble organic phosphorus (III) compounds in complex-bound form, of group VII of the Periodic Table of the Elements at temperatures of from 70 to 150° C. and pressures of from 0.5 to 10 MPa, with synthesis gas to give 8(9)-formyltricyclo[5.2.1.0$^{2,6}$]dec-3-ene, then separating the organic phase from the aqueous phase and subsequently converting the thus obtained 8(9)-formyltricyclo[5.2.1.0$^{2,6}$]dec-3-ene, in a second hydroformylation stage in homogeneous organic phase in the presence of transition metal compounds of group VII of the Periodic Table of the Elements at temperatures of from 70 to 140° C. and pressures of from 5 to 35 MPa by reacting with synthesis gas, to 3(4),8(9)-bisformyltricyclo[5.2.1.0$^{2,6}$]decane and subsequently reductively aminating the thus obtained 3(4),8(9)-bis-formyltricyclo[5.2.1.0$^{2,6}$]decane to give 3(4),8(9)-bis(aminomethyl) tricyclo-[5.2.1.0$^{2,6}$]decane.

A characteristic of the inventive process for hydroformylating dicyclopentadiene is the two-stage reaction management, the first stage working by the heterogeneous biphasic process in the presence of an aqueous catalyst solution and the reaction product of the first stage, comprising predominantly TCD-monoaldehyde and small amounts of unconverted DCP, being converted without further purification, in a second stage after addition of catalyst in a homogeneous reaction medium, to TCD-dialdehyde, which is subsequently reductively aminated to give TCD-diamine. This type of reaction management results in very selective hydroformylation of the double bond present in the six-membered ring of the TCD structure in the first reaction stage to give TCD-monoaldehyde, which is frequently also referred to as TCD-monenal {8(9)-formyltricyclo[5.2.1.0$^{2,6}$]dec-3-ene}.

It is found that, surprisingly, the reaction product of the first hydroformylation stage can be hydroformylated to the TCD-dialdehyde after removing the aqueous catalyst phase without further purification in a homogeneous organic medium after addition of catalyst, even though the organic phase comprising the product of value comprises homogeneously dissolved and analytically detectable amounts of phosphorus and sulfur dissociation and decomposition products which are known to be catalyst poisons in the oxo process.

According to "New Synthesis with Carbon Monoxide" (Edited by J. Falbe, Springer-Verlag 1980, Reactivity and Structure Concepts in Organic Chemistry, Vol. 11, page 73), numerous catalyst poisons are known in rhodium-catalyzed hydroformylation. In addition to halogen, acetylenes and carboxylic acids, reference is made in particular to sulfur. Even small amounts of these catalyst poisons bring about a drastic deactivation of the hydroformylation catalyst.

For the subsequent reaction step too, the crude TCD-dialdehyde product may be used without intermediate purification steps, for example distillation or wash steps. The reductive amination of TCD-dialdehyde to TCD-diamine is effected by conventional processes.

This is surprising inasmuch as numerous publications describe the influence of catalyst poisons on hydrogenation processes carried out over fixed bed catalysts in industry. Ullmann's Encyclopedia of Industrial Chemistry, 5th edition, 1985, Vol. A1, page 283 refers to the effect of sulfur-containing catalyst poisons on heterogeneously catalyzed hydrogenation processes.

Moreover, DE-B 29 18 107 refers to a distillative purification of the unsaturated aldehyde before further processing of TCD-monenal {8(9)-formyltricyclo[5.2.1.0$^{2,6}$]dec-3-ene} to the corresponding saturated aldehyde TCD-monal.

The teaching in DE-B 26 54 221 too refers to the use of TCD-monenal worked up distillatively for the subsequent hydrogenation step.

It has likewise been found that, surprisingly, dicyclopentadiene which has not been fully converted in the first stage can be converted to the TCD-dialdehyde in the second hydroformylation stage without formation of high-boiling by-products. From this arises the advantageous possibility of a partial DCP conversion method in the first hydroformylation stage.

However, a distillative purification of TCD-monenal from the removed organic phase of the first hydroformylation stage is not ruled out. This procedure does, though, require an additional distillation step and leads to distillation losses, even if they are only small. The selective preparation of TCD-monenal from dicyclopentadiene using an aqueous catalyst solution and the distiliative purification is disclosed by EP-B1-0 186 075.

The first reaction stage of the novel process is carried out as a heterogeneous reaction in a biphasic system, a reaction which is described, for example, in DE-B-26 27 354. This process is characterized by the presence of an organic phase which comprises the olefinic starting material and the reaction product, and an aqueous phase in which the catalyst is dissolved. The catalysts used are water-soluble rhodium complexes which contain water-soluble organic phosphorus (III) compounds as ligands. Examples of water-soluble phosphorus (III) compounds which form complexes with rhodium are triarylphosphines, trialkylphosphines, mixed aliphatic-aromatic phosphines and arylated or alkylated diphosphines whose organic radicals contain sulfonic acid groups or carboxyl groups. Their preparation and use are disclosed, for example, by DE-B 26 27 354, EP-B1-0 103 810, EP-B1-0 163 234 and EP-A1-0 571 819. Further groups of suitable compounds are sulfonated or carboxylated organic phosphites, and heterocyclic compounds of trivalent phosphorus, which are disclosed, for example, by EP-A1-0 575 785 and EP-A1-0 646 588.

Suitable sulfonated arylphosphines in the process according to the invention are sulfonated triarylphosphines of the formula (I)

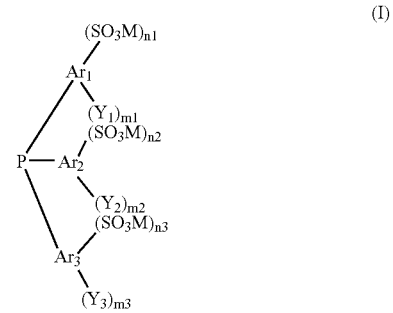

in which $Ar^1$, $Ar^2$ and $Ar^3$ are identical or different aryl groups having from 6 to 14 carbon atoms, the substituents $Y_1$, $Y_2$ and $Y_3$ are identical or different, straight-chain or branched alkyl or alkoxy radicals having from 1 to 4 carbon atoms, chlorine, bromine, the hydroxyl, cyanide or nitro group, and also the amino group of the formula $NR^1R^2$ in which the substituents $R^1$ and $R^2$ are the same or different and are each hydrogen, straight-chain or branched alkyl groups having from 1 to 4 carbon atoms, in which M is lithium, sodium, potassium, magnesium, calcium or barium, in which $m_1$, $m_2$ and $m_3$ are the same or different and are each integers from 0 to 5, in which $n_1$, $n_2$ and $n_3$ are the same or different and are each integers from 0 to 3, and at least one of the numbers $n_1$, $n_2$ and $n_3$ is equal to or greater than 1.

The triarylphosphines preferably include those triarylphosphines in which the $Ar^1$, $Ar^2$, $Ar^3$ groups are phenyl groups; $Y_1$, $Y_2$ and $Y_3$ are the methyl, the ethyl group, the methoxy, ethoxy group and/or a chlorine atom; and the cationic M radicals are inorganic cations of sodium, potassium, calcium and barium. Especially suitable are those triarylphosphines in which $Ar^1$, $Ar^2$, $Ar^3$ are each a phenyl group, $m_1$, $m_2$, $m_3$ are each 0, $n_1$, $n_2$ and $n_3$ are each 0 or 1 and $n_1+n_2+n_3$ together add up to from 1 to 3, and in which the sulfonate groups are in the meta-position.

A mixture, suitable for carrying out the hydroformylation process according to the invention, of (sulfophenyl)diphenylphosphine, di(sulfophenyl)phenylphosphine and tri(sulfophenylphosphine) is obtained in the sulfonation of triphenylphosphine, as disclosed, for example, by DE-A 26 27 354. In the prior art, (sulfophenyl)diphenylphosphine is abbreviated to TPPMS, di(sulfophenyl)phenylphosphine to TPPDS and tri(sulfophenyl)phosphine to TPPTS.

Suitable sulfonated arylphosphines are likewise sulfonated diphosphines of the formulae (II) or (III)

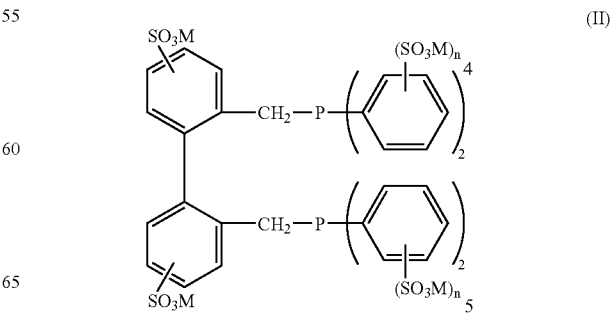

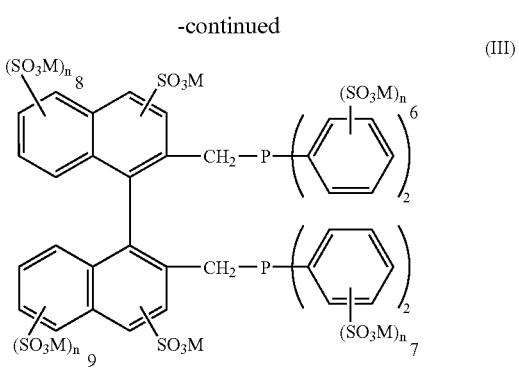

These diphosphines of the formulae (II) and (III) are disclosed by WO 98/30526.

In (II), each $n_4$ and $n_5$ is independently 0 or 1, and the compound of the formula (II) contains up to six —$SO_3M$ groups.

In (III), each $n_6$, $n_7$, $n_8$ and $n_9$ is independently 0 or 1, and the compound of the formula (III) contains from four to eight —$SO_3M$ groups.

As a consequence of the preparation by sulfonation of the corresponding diphosphines of the formulae (IIa) and (IIIa) which contain no —$SO_3M$ groups

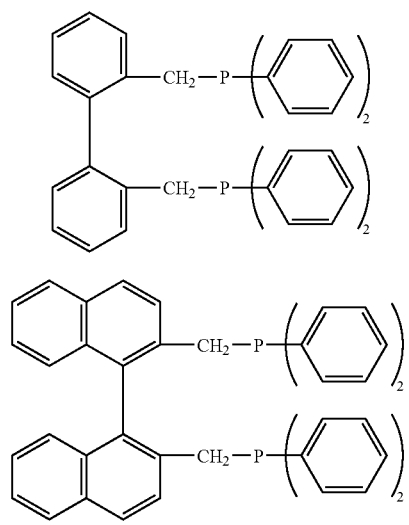

mixtures of compounds (II) and (III) with a different number of —$SO_3M$ groups are typically obtained. For instance, a compound of the formulae (II) or (III) which contains, for example, three —$SO_3M$ groups also contains compounds having only two —$SO_3M$ groups, but also compounds having four or five —$SO_3M$ groups. A compound of the formulae (II) or (III) having, for example, five —$SO_3M$ groups typically also contains compounds having only three or four —$SO_3M$ groups, but also compounds having six or seven —$SO_3M$ groups.

Compounds of the formula (II) have a maximum of six —$SO_3M$ groups, while compounds of the formula (III) have a maximum of eight —$SO_3M$ groups.

For this reason, mixtures of compounds of the formulae (II) and (III) having a different number of —$SO_3M$ groups are generally used.

In the formulae (II) and (III), M is ammonium, a monovalent metal or the equivalent of a polyvalent metal, especially sodium, potassium, calcium or barium.

It is particularly advantageous to use water-soluble complexes of rhodium, although the use of other catalytically active transition metal compounds of group VIII of the Periodic Table of the Elements is not ruled out. For instance, in the first hydroformylation stage, it is also possible to use water-soluble complexes of cobalt, iridium, nickel, palladium, platinum, iron or ruthenium, and particularly water-soluble complexes of cobalt, iridium and platinum have been found to be effective as hydroformylation catalysts.

The conditions under which the conversion in the first hydroformylation stage proceeds may vary within wide limits and be adapted to the individual circumstances. They depend, inter alia, upon the starting material, upon the catalyst system selected and upon the desired degree of conversion.

Typically, the hydroformylation of the starting materials is carried out at temperatures of from 70 to 150° C. Preference is given to maintaining temperatures of from 100 to 150° C. and especially from 110 to 140° C. The overall pressure extends over a range of from 0.5 to 10 MPa, preferably from 1 to 6 MPa and especially from 1.5 to 5 MPa. The molar ratio of hydrogen to carbon monoxide varies typically between 1:10 and 10:1; mixtures which contain hydrogen and carbon monoxide in a molar ratio of from 3:1 to 1:3, especially about 1:1, are particularly suitable.

The rhodium concentration is from 20 to 1000 ppm by weight, preferably from 50 to 800 ppm by weight and especially from 100 to 600 ppm by weight, based in each case on the aqueous catalyst solution. Although it is possible to use the rhodium-phosphorus complex having stoichiometric composition as the catalyst, it is customary to work in the presence of excess phosphorus ligand, i.e. ligand which has not entered into complexation with rhodium. Per mole of rhodium, preference is given to using from 10 to 300 mol of phosphorus in the form of a water-soluble organic phosphorus compound. Particularly favorable molar ratios of rhodium to phosphorus have been found to be in the range from 1:50 to 1:150. The rhodium-phosphorus complex catalyst does not need to have a uniform composition, but rather may consist, for example, of a mixture of rhodium complexes which differ by the type of the phosphorus ligands. Equally, the free phosphorus ligand present in the aqueous catalyst solution may be composed of a mixture of different water-soluble organic phosphorus compounds.

When the catalytically active metal used is another transition metal of group VIII of the Periodic Table of the Elements, the concentration of transition metal and the molar ratio of transition metal to phosphorus vary within the ranges which are selected in the case of rhodium. The optimal values in each case can be determined by simple routine experiments as a function of the particular transition metal used.

The catalyst is typically formed from the components of transition metal or transition metal compound, organic phosphorus compound and synthesis gas under the conditions of the hydroformylation reaction in the reaction mixture. However, it is also possible to initially preform the catalyst and subsequently feed it to the actual hydroformylation stage. The conditions of the preformation generally corresponds to the hydroformylation conditions.

Dicyclopentadiene may be fed to the hydroformylation as such or in solution. Suitable solvents are water-insoluble ketones, dialkyl ethers, aliphatic nitriles, aromatic hydrocarbons such as benzene or toluene and saturated cycloaliphatic hydrocarbons such as cyclopentane or cyclohexane, or saturated aliphatic hydrocarbons.

In order to increase the conversion per unit time of dicyclopentadiene which only has low solubility in the aqueous catalyst solution, it may be advisable to add to this solution a phase transfer reagent (solubilizer). It changes the physical properties of the interfaces between the two liquid phases and eases the transfer of the organic reactants into the aqueous catalyst solution.

Solubilizers refer to compounds whose hydrophilic groups are ionic (anionic or cationic) or nonionic. The anion-active compounds include sodium, potassium or ammonium salts of carboxylic acids, preferably those having from 8 to 20 carbon atoms and especially of saturated fatty acids having from 12 to 18 carbon atoms, and also alkyl sulfates, alkylbenzene-sulfonates and alkylbenzene phosphates. Examples of cationic solubilizers are tetraalkylammonium and N-alkylpyridinium salts. The nonionic phase transfer reagents do not dissociate into ions in aqueous solution. They include alkylpolyethylene glycols, alkylphenylpolyethylene glycols, fatty acid alkylolamines and trialkylamine oxides. In addition, ampholytes such as amino carboxylic acids, betaines and sulfobetaine are in use as solubilizers. Corresponding processes are disclosed, for example, by EP-B1-0 157 316.

It is also possible to use rhodium complexes which are simultaneously catalyst and phase transfer reagent. Such a procedure is, for example, the subject matter of EP-B1-0 163 234.

Also with regard to the process technology and apparatus configuration of the first stage of the novel process, it is possible to vary within wide limits. A proven embodiment of the heterogeneous hydroformylation using an aqueous catalyst phase is described in EP-B1-0 103 810. The reaction effluent of the first hydroformylation stage is separated in a phase separator into the organic product phase and into the aqueous catalyst solution. It has been found to be appropriate to circulate the catalyst solution. The crude organic product phase is fed to the second hydroformylation stage without further purification steps. However, an intermediate distillative purification of the reaction product of the first hydroformylation stage may optionally also be carried out.

The second hydroformylation stage of the novel process is carried out in a homogeneous reaction system. The term homogeneous reaction system represents a homogeneous solution composed substantially of solvent, if added in the first stage and/or in the second reaction stage, catalyst, unconverted dicyclopentadiene and TCD-monenal. In some cases, an addition of solvent in the second reaction stage may be found to be appropriate. The solvents used are organic compounds in which starting material, reaction product and catalyst system are soluble. Examples of such compounds are aromatic hydrocarbons such as benzene and toluene or the isomeric xylenes and mesitylene. Other customary solvents are paraffin oil, cyclohexane, n-hexane, n-heptane or n-octane, ethers such as tetrahydrofuran, ketones or Texanol® from Eastman. The proportion of the solvent in the reaction medium may be varied over a wide range and is typically between 10 and 80% by weight, preferably from 20 to 50% by weight, based on the reaction mixture.

However, an addition of solvent in the second, just like in the first hydroformylation stage, is not necessarily required.

The catalysts used in the second hydroformylation stage are transition metal compounds of group VIII of the Periodic Table of the Elements, preferably compounds of cobalt, rhodium, iridium, nickel, iron, platinum, palladium or ruthenium and especially of cobalt, rhodium and iridium.

Particular preference is given to using rhodium. The rhodium compounds used are generally not modified with phosphorus ligands such as phosphines or phosphites. Those rhodium catalysts not modified with phosphines or phosphites and their suitability as a catalyst for hydroformylation are disclosed by the literature and they are referred to as unmodified rhodium catalysts. The technical literature assumes that the rhodium compound $HRh(CO)_4$ is the catalytically active rhodium species in the hydroformylation with unmodified rhodium catalysts, even though this has not been proved unambiguously as a consequence of the many chemisms proceeding in parallel in the hydroformylation zone. Since the use of rhodium catalysts not modified with phosphines generally entails a relatively low rhodium content, preference is given to working in the second hydroformylation stage with unmodified rhodium catalysts. The rhodium content is generally from 5 to 100 ppm, based on the homogeneous reaction mixture.

However, it is also possible in the second hydroformylation stage to use rhodium complexes which contain organic phosphorus (III) compounds as ligands. Such complexes and their preparation are known (for example from U.S. Pat. Nos. 3,527,809, 4,148,830, 4,247,486, 4,283,562). They may be used as single complexes or else as a mixture of different complexes. The rhodium concentration in the reaction medium extends over a range of from about 5 to about 1000 ppm by weight and is preferably from 10 to 700 ppm by weight. In particular, rhodium is used in concentrations of from 20 to 500 ppm by weight, based in each case on the homogeneous reaction mixture. The catalysts used may be the rhodium complex having a stoichiometric composition. However, it has been found to be appropriate to carry out the hydroformylation in the presence of a catalyst system composed of rhodium-phosphorus complex and free, i.e. excess, phosphorus ligands, which no longer enters into complexation with rhodium. The free phosphorus ligand may be the same as in the rhodium complex, but it may also be possible to use ligands different therefrom. The free ligand may be a single compound or consist of a mixture of different organophosphorus compounds. Examples of rhodium-phosphorus complexes which may find use as catalysts are described in U.S. Pat. No. 3,527,809. The preferred ligands in the rhodium complex catalysts include, for example, triarylphosphines such as triphenylphosphine, trialkylphosphines such as tri(n-octyl)phosphine, trilaurylphosphine, tri(cyclohexyl)phosphine, alkylphenylphosphines, cycloalkylphenylphosphines and organic diphosphites. Owing to its ease of obtainability, triphenylphosphine is employed particularly frequently.

When operation is effected with a modified rhodium complex catalyst system, the molar ratio of rhodium to phosphorus in the homogeneous reaction mixture is typically from 1:5 to 1:200, but the molar proportion of phosphorus in the form of organic phosphorus compounds may also be higher. Preference is given to using rhodium and organically bonded phosphorus in molar ratios of from 1:10 to 1:100.

When a transition metal of group VIII of the Periodic Table of the Elements other than rhodium is used in the second hydroformylation stage, the concentration of transition metal and the molar ratio of transition metal to phosphorus, if operation is effected by the phosphine-modified process, is within the ranges which are also selected in the case of rhodium. The optimal values in each case can be determined by simple routine experiments as a function of the transition metal used in each case.

The conditions under which the reaction in the second hydroformylation stage proceeds may vary within wide limits and be adapted to the individual circumstances. They depend, inter alia, upon the starting material, upon the catalyst system selected and upon the desired degree of conversion. Typically, the second hydroformylation stage of the crude TCD-monenal is carried out at temperatures of from 70 to 140° C. Preference is given to maintaining temperatures of from 80 to 130° C. and especially from 90 to 120° C. The total pressure extends over a range of from 5 to 35 MPa, preferably from 10 to 30 MPa and especially from 20 to 30 MPa. The molar ratio of hydrogen to carbon monoxide varies typically between 1:10 and 10:1; mixtures which contain hydrogen and carbon monoxide in a molar ratio of from 3:1 to 1:3, especially about 1:1, are particularly suitable.

The catalyst is typically formed from the components of transition metal or transition metal compound and synthesis gas under the conditions of the hydroformylation reaction in the reaction mixture, optionally in the presence of organic phosphorus (III) compounds. However, it is also possible to initially preform the catalyst and subsequently feed it to the actual hydroformylation stage. The conditions of the preformation generally correspond to the hydroformylation conditions.

To prepare the hydroformylation catalyst for the first and second reaction stage, the transition metal of group VIII of the Periodic Table of the Elements, especially rhodium, is used either in metallic form or as a compound. In the metallic form, the transition metal is used either in the form of finely divided particles or precipitated in a thin film on a support such as activated carbon, calcium carbonate, aluminium silicate, clay earth. Suitable transition metals are salts of aliphatic mono- and polycarboxylic acids, such as transition metal 2-ethylhexanoates, acetates, oxalates, propionates or malonates. In addition, salts of inorganic hydrogen and oxygen acids may be used, such as nitrates or sulfates, the different transition metal oxides or else transition metal carbonyl compounds such as $Rh_3(CO)_{12}$, $Rh_6(CO)_{16}$, $Co_2(CO)_8$, $Co_4(CO)_{16}$, $Fe(CO)_5$, $Fe_2(CO)_9$, $Ir_2(CO)_8$, $Ir_4(CO)_{12}$ or transition metal complexes, for example cyclo-pentadienyl-rhodium compounds, rhodium acetylacetonate, (1,5-cyclo-octadienyl)cyclopentadienecobalt, (1,5-cyclooctadienyl)Fe(CO)$_3$, [(1,5-cyclooctadienyl)RhCl]2 or (1,5-cyclooctadienyl)PtCl$_2$. Owing to their corrosive behavior of the halide ions, transition metal halide compounds are less useful.

Preference is given to using transition metal oxides and especially transition metal acetates and 2-ethylhexanoates. It has been found that rhodium oxide, rhodium acetate, rhodium 2-ethylhexanoate, cobalt oxide, cobalt acetate and cobalt 2-ethylhexanoate are particularly suitable.

The individual hydroformylation stages may be carried out either batchwise or continuously.

The reaction product of the second hydroformylation stage is reductively aminated without further purification and without catalyst removal.

Reductive amination refers to the reaction of TCD-dialdehyde with hydrogen and ammonia in the presence of a hydrogenation catalyst. However, the dialdehyde may also initially be reacted with a primary amine to form a diazomethine and the diazomethine thereupon treated with hydrogen and ammonia in the presence of a hydrogenation catalyst. In the context of the invention, this reaction is also referred to as reductive amination.

To form the diazomethine, from 2 to 6 mol, in particular from 3 to 4 mol, of a primary amine are added per mole of tricyclodecanedialdehyde to the hydroformylation mixture which has not been worked up. The reaction between the starting materials proceeds even at room temperature; it can be accelerated by heating to from 20 to 60° C., in particular from 30 to 50° C. Suitable primary amines are amines having from 2 to 10 carbon atoms in the molecule. With particular success, amines having from 3 to 5 carbon atoms in the molecule, preferably n-butylamine, are used.

The reductive amination of the dialdehyde or of the diazomethine is appropriately carried out at temperatures of from 60 to 150° C., preferably from 80 to 140° C. The hydrogen pressure in the reaction vessel at the reaction temperature is from 2 to 12 MPa and in particular from 8 to 10 MPa.

The hydrogenation catalysts used are nickel or cobalt, either in the form of Raney nickel or Raney cobalt, or else in the form of corresponding supported catalysts. A preferred catalyst contains from 50 to 60% by weight of nickel on kieselguhr.

Ammonia should appropriately be used in excess. Per mole of formyl group or per mole of diazomethine group, at least 2 mol of ammonia are required; preference is given to using from 4 to 10 mol of ammonia.

The reductive amination of the dialdehyde or of the diazomethine may be carried out in the absence of solvents; the end product itself typically acts as a solvent. However, in the case of small batches, it is advantageous to work in a solvent. Particularly good results are achieved when tetrahydrofuran, isobutanol, butanol or isopropanol is used as the solvent.

The mixture of the isomeric diamines is obtained in good yields. Only a small portion of the dialdehydes is converted to higher molecular weight condensation products. They are dissolved in the reaction mixture and do not disrupt the withdrawal of product from the reactor or trouble-free workup of the crude products.

To remove the isomeric TCD-diamines, the reaction mixture is distilled, preferably under reduced pressure. The compounds are obtained as a colorless liquid which boil at about 310° C. under atmospheric pressure. The hydrogenation catalyst and the transition metal used in the second hydroformylation-stage are obtained in the distillation residue and are recovered by known processes.

The novel process is illustrated in detail in the examples which follow. It will be appreciated that the intention is not to restrict the invention to these specific embodiments.

EXAMPLES

The abbreviations used in the analytical characterization of the reaction products are defined as follows:

| | |
|---|---|
| DCP | dicyclopentadiene |
| TCD-monenal | 8(9)-formyltricyclo[5.2.1.0$^{2,6}$]dec-3-ene |
| TCD-dial | 3(4),8(9)-bisformyltricyclo[5.2.1.0$^{2,6}$]decane |
| Tri-CP | tricyclopentadiene |
| TPPTS means | sodium triphenylphosphinetrisulfonate |

Preparation of TCD-diamine

1. Preparation of TCD-Monenal

A 5 l autoclave is initially charged with 2,119 g of TPPTS solution having a P(III) content of 472 mmol/kg which are admixed with 160.2 g of Rh solution (Rh content: 6,423 mg/kg). Afterward, a mixture of 661.1 g of dicyclopentadiene (technical grade, DCP content: 93.72% by weight) and 283.0 g of toluene is added. The reaction mixture is heated to 135° C. and converted at a synthesis gas pressure of 2.5 MPa and a reaction time of 6 hours.

After the end of the reaction, the mixture is cooled and the other, organic phase is removed from the aqueous catalyst phase by phase separation. The remaining catalyst phase is again admixed with a mixture of dicyclopentadiene and toluene and again converted. This procedure is repeated a total of eight times.

The organic phases (sum: 9,923 g) are combined and analyzed by gas chromatography.

GC Analysis (in area %)

| First runnings components | 0.32 |
| Toluene | 29.45 |
| DCP | 4.55 |
| TCD-monenal | 61.30 |
| TCD-dial | 0.81 |
| Tri-CP | 0.42 |
| Others | 3.15 |

2. Preparation of TCD-dialdehyde 400 g of crude TCD-monenal from the first reaction stage, without employing further purification steps, are adjusted to a rhodium content of 20 ppm based on the entire reaction solution by adding a toluenic solution of rhodium 2-ethylhexanoate, and initially charged in a 1 l autoclave. The reaction mixture is heated to 120° C. and converted at a pressure of 26.0 MPa and a reaction time of 6 hours. After the end of the reaction, the mixture is cooled and decompressed, and the resulting reaction product (455.9 g) is analyzed by gas chromatography.

GC Analysis (in area %)

| First runnings components | 1.30 |
| Toluene | 31.70 |
| TCD-monenal | 2.32 |
| TCD-dial | 62.36 |
| Others | 2.32 |

3. Preparation of TCD-diamine

The TCD-dialdehyde obtained after the second hydroformylation stage is used in the reductive amination without further purification. To this end, 242.0 g of n-butylamine are initially charged in a 1 l three-neck flask with stirrer. 400.0 g of TCD-dialdehyde are added dropwise at a temperature of 42-45° C. within 90 minutes. The mixture is stirred at 40-45° C. for two further hours, then allowed to cool and the aqueous phase which occurs (62.2 g) is separated from the organic phase (579.8 g) (Schiff base). 100.0 g of toluene and 45.0 g of Ni 52/35 catalyst from Johnson-Matthey plc are then initially charged in a 2 l autoclave, 550.0 g of ammonia are pumped into this mixture and the mixture is heated to 50° C. Subsequently, the Schiff base formed beforehand from the reaction between TCD-dialdehyde and n-butylamine is pumped in within 2 hours and the reaction mixture is heated to 120° C. under hydrogen and reacted at a pressure of 10.0 MPa and a reaction time of 6 hours. After the end of the reaction, the mixture is cooled and decompressed, and the catalyst is filtered off. The thus obtained reaction product (736.2 g) is analyzed by gas chromatography.

GC Analysis (in area %)

| First runnings components | 0.28 |
| n-Butylamine | 26.08 |
| Toluene/methylcyclohexane | 38.80 |
| TCD-monoamine | 1.92 |
| TCD-diamine | 31.52 |
| Others | 1.40 |

For the workup, the crude TCD-diamine (700.0 g) is distilled on a Claisen head with condenser. 250.6 g of main fraction are obtained in a boiling range of 115-129° C. at a pressure of 3 hPa with the following composition.

GC Analysis (in area %)

| First runnings components | 0.11 |
| TCD-monoamine | 4.02 |
| TCD-diamine | 95.46 |
| Others | 0.41 |

The overall yield of TCD-diamine over all stages is 86.8% of theory, based on dicyclopentadiene. TCD-monoamine means the monofunctional amine 8(9)-aminomethyltricyclo[5.2.1.0$^{2,6}$]decane.

The process according to the invention opens up an elegant preparative route for TCD-diamine in high yields, and allows the complicated purification of the intermediates to be dispensed with.

What we claim is:

1. A process for preparing 3(4),8(9)-bis(aminomethyl)tricycle-[5.2.1.0$^{2,6}$]decane by hydroformylating dicyclopentadiene with subsequent reductive amination, comprising reacting dicyclopentadiene, in a first hydroformylation stage in a heterogeneous reaction system using an aqueous solution of transition metal compounds, containing water-soluble organic phosphorus (III) compounds in complex-bound form selected from the group consisting of sulfonated triarylphosphines of the formula (I)

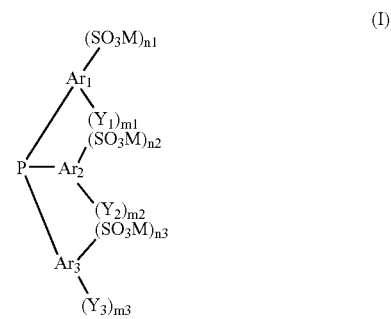

in which $Ar^1$, $Ar^2$ and $Ar^3$ are individually aryl groups of 6 to 14 carbon atoms, the substituents $Y_1$, $Y_2$ and $Y_3$ are individually selected from the group consisting of alkyl and alkoxy of 1 to 4 carbon atoms, chlorine, bromine, hydroxyl, cyanide, nitro, and $NR^1R^2$ in which the $R^1$ and $R^2$ are individually hydrogen, or alkyl of 1 to 4 carbon atoms, in which m is selected from the group consisting of lithium, sodium, potassium magnesium, calcium and barium, $m_1$, $m_2$, and $m_3$ are individually integers from 0 to 5, $n_1$, $n_2$, $n_3$ are individually integers from 0 to 3, and at least one of $n_1$, $n_2$ and $n_3$ equal to or treater than 1; sulfonated diphosphines of the formula (II)

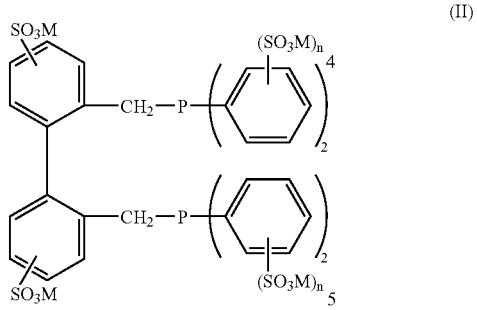
(II)

in which $n_4$ and $n_5$ are individually 0 to 1, and the sulfonated diphosphines of the formula (II) up to six $SO_3M$ groups, and M is selected from the group consisting of ammonium, a monovalent metal and an equivalent of a polyvalent metal and; sulfonated diphosphines of the formula (III)

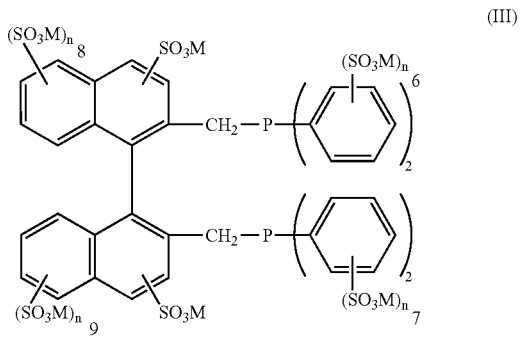
(III)

in which $n_6$, $n_7$, $n_8$ and $n_9$ are individually 0 or 1, and the sulfonated diphosphines of the formula (III) contain from four to eight $SO_3M$ groups, and M is selected from the group consisting of ammonium, a monovalent metal and an equivalent of a polyvalent metal; of group VIII of the Periodic Table of the Elements at temperatures of from 70 to 150° C. and pressures of from 0.5 to 10 MPa, with hydrogen and carbon monoxide to give 8(9)-formyltricyclo[5.2.1.0$^{2,6}$]dec-3-ene, then separating the organic phase from the aqueous phase and subsequently converting the thus obtained 8(9)-formyltricyclo[5.2.1.0$^{2,6}$]dec-3-ene, in a second hydroformylation stage in a homogeneous organic phase in the presence of transition metal compounds of group VIII of the Periodic Table of Elements at temperatures of from 70 to 140° C. and pressures of from 5 to 35 MPa by reacting with hydrogen and carbon monoxide, to 3(4),8(9)-bisformyltricyclo[5.2.1.0$^{2,6}$]decane and subsequently reductively aminating the thus obtained 3(4),8(9)-bisformyltricyclo-[5.2.1.0$^{2,6}$]decane to give 3(4),8(9)-bis(aminomethyl) tricyclo[5.2.1.0$^{2,6}$]decane.

2. The process as claimed in claim 1, wherein 8(9)-formyl-tricyclo[5.2.1.0$^{2,6}$]dec-3-ene obtained in the first hydroformylation stage is distilled before use in the second hydroformylation stage.

3. The process as claimed in claim 1, wherein, in the second hydroformylation stage, the reaction is effected in the presence of organic phosphorus (III) compounds.

4. The process as claimed in claim 1, wherein in formula (I), $Ar_1$, $Ar_2$ and $Ar_3$ are phenyl, $m_1$, $m_2$, $m_3$ are each 0, $n_1$, $n_2$, $n_3$ are each 0 or 1 and $n_1+n_2+n_3$ together add up to 1 to 3, and the sulfonate groups are in the meta-position.

5. The process of claim 1, wherein the transition metal compounds, used in the first hydroformylation stage, of group VIII of the Periodic Tale of the Elements are compounds of a member selected from the group consisting of rhodium, cobalt, iridium, nickel, palladium, platinum, iron and ruthenium.

6. The process of claim 1, wherein the transition metal compounds, used in the second hydroformylation stage, of group VIII of the Periodic Table of the Elements are compounds of a member of the group consisting of rhodium, cobalt, iridium, nickel, platinum, palladium, iron and ruthenium.

7. The process of claim 1, wherein the transition metal compounds, used in the first and second hydroformylation stage, of group VIII of the Periodic Table of the Elements are compounds of rhodium.

8. The process of claim 1, wherein the temperature in the first hydroformylation stage is from 100 to 150° C., and the pressure is from 1 to 6 MPa.

9. The process of claim 1, wherein the temperature in the second hydroformylation stage is from 80 to 130° C., and the pressure is from 10 to 30 MPa.

10. The process of claim 7, wherein the rhodium concentration in the first hydroformylation stage is from 20 to 1000 ppm by weight, based in each case on the aqueous catalyst solution.

11. The process of claim 1, wherein from 10 to 300 mol of phosphorus in the form of the water-soluble organic phosphorus compound are used per mole of rhodium in the first hydroformylation stage.

12. The process of claim 7, wherein the rhodium concentration in the second hydroformylation stage is from 5 to 100 ppm by weight, based on the homogeneous reaction mixture.

13. The process of claim 11, wherein the rhodium concentration in the second hydroformylation stage is from 5 to 1000 ppm by weight, based in each case on the homogeneous reaction mixture, and from 5 to 200 mol of phosphorus in the form of organic phosphorus compounds are used per mole of rhodium.

* * * * *